(12) United States Patent
Nadadur et al.

(10) Patent No.: US 7,775,978 B2
(45) Date of Patent: Aug. 17, 2010

(54) CYCLICAL INFORMATION DETERMINATION WITH MEDICAL DIAGNOSTIC ULTRASOUND

(75) Inventors: Desikachari Nadadur, Issaquah, WA (US); Anil V. Relkuntwar, Redmond, WA (US); Mervin Mencias Smith-Casem, Bellevue, WA (US); Timothy Thigpen, Portland, OR (US); Carol M. Lowery, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1184 days.

(21) Appl. No.: 11/076,791

(22) Filed: Mar. 9, 2005

(65) Prior Publication Data

US 2006/0241457 A1     Oct. 26, 2006

(51) Int. Cl.
*A61B 8/00* (2006.01)
(52) U.S. Cl. ........................ 600/437; 382/128; 382/131; 128/922
(58) Field of Classification Search ................. 600/437; 382/173, 131, 128; 128/922; 377/10, 11, 377/12
See application file for complete search history.

(56) References Cited

U.S. PATENT DOCUMENTS

| | | | |
|---|---|---|---|
| 6,086,539 A * | 7/2000 | Guracar et al. ............... 600/453 |
| 6,224,553 B1 * | 5/2001 | Nevo ........................... 600/437 |
| 6,312,382 B1 * | 11/2001 | Mucci et al. ................. 600/437 |
| 6,322,505 B1 * | 11/2001 | Hossack et al. ............. 600/437 |
| 6,673,017 B1 | 1/2004 | Jackson |
| 7,031,504 B1 * | 4/2006 | Argiro et al. ................. 382/131 |
| 2003/0016851 A1 * | 1/2003 | Kaufman et al. ............ 382/131 |
| 2004/0086197 A1 * | 5/2004 | Fletcher et al. ............. 382/276 |
| 2005/0033123 A1 | 2/2005 | Gardner et al. |
| 2005/0033179 A1 | 2/2005 | Gardner et al. |
| 2005/0107704 A1 | 5/2005 | Von Behren |
| 2005/0203395 A1 * | 9/2005 | Sui et al. ..................... 600/437 |
| 2005/0228287 A1 * | 10/2005 | Little et al. ................. 600/459 |
| 2005/0288585 A1 | 12/2005 | Zamboglu |
| 2006/0034513 A1 * | 2/2006 | Cai et al. ..................... 382/173 |
| 2008/0130964 A1 * | 6/2008 | Zwirn et al. ................. 382/128 |

\* cited by examiner

*Primary Examiner*—Long V Le
*Assistant Examiner*—Nigel Fontenot

(57) ABSTRACT

Without using ECG input signals or processor intensive correlation, cyclical timing is determined from ultrasound data. Cyclical timing includes determining the time of end diastole, time of end systole or heart rate. The ultrasound data is reduced, such as by projecting each frame of data onto two axes. For projection, data is summed along each dimension. The location associated with the maximum variance through the sequence is identified from the projected data. The ultrasound data associated with the location is used to identify cycle timing information, such as to provide a waveform representing the cycle. Lines from different frames of data in the sequence are also used to generate an image. The image shows cycle timing information.

26 Claims, 2 Drawing Sheets

CYCLICAL INFORMATION DETERMINATION WITH MEDICAL DIAGNOSTIC ULTRASOUND

BACKGROUND

The present invention relates to determining cycle information with medical diagnostic ultrasound data. In particular, cyclic events are identified with ultrasound data and without an ECG input.

Knowledge of the end-diastolic (ED) and end-systolic (ES) image frame locations in a cardiac cycle allows for quantitative evaluation of the left-ventricular (LV) function using measures such as ejection fraction (EF), stroke volume (SV), or cardiac output (CO). These measures depend on the volumes enclosed by the LV walls at ED and ES time. At the ED time, the LV has the largest enclosed volume, and, at ES time, the LV has the smallest enclosed volume.

Traditionally, identification of these two frames in a cardiac cycle is carried out manually. A user scrolls through or plays a sequence of 2D image frames of a cardiac cycle in a loop and marks the image frame corresponding to the largest area of the LV cross-section as the ED frame and that with the smallest area of the LV cross-section as the ES frame. Given an ECG signal, the ED frame may be identified as the frame that falls immediately after the R-wave peak, but the ES frame is detected manually. Manual identification can be subjective and time consuming. Manual identification also typically occurs after an image sequence is obtained and saved, limiting the ability to alter the acquisition of data based on identification of cycle timing information. Occasionally, an ECG sensor or input signal is not available to reduce the amount of manual identification.

A formula may be used to compute the ES time or duration of the LV ejection fraction (LVEF). The formulas may replace the manual searching of the ES image frame. In milliseconds and given the heart rate (HR) and gender, the formulas are:

Male: $HR \times (-1.7) + 413$, (1)

Female: $HR \times (-1.6) + 418$, (2)

where HR is the heart rate. The approximate location of the ES frame of data is determined by looking at the timestamps on the image frames. These formulas give good results with heart rates up to about 120 to 150 beats per minute (bpm). For higher heart rates, the formulas tend to produce intervals that are too short.

BRIEF SUMMARY

By way of introduction, the preferred embodiments described below include a method, computer readable media and systems for determining cyclical information from ultrasound data. Without using ECG input signals or processor intensive pattern matching or correlation, cyclical timing is determined, such as determining the time of ED, time of ES or heart rate. The ultrasound data is reduced, such as by projecting each frame of data onto two axes. Data is summed along each dimension. The location associated with the maximum variance through the sequence is identified from the projected data. The ultrasound data associated with the location is used to identify cycle timing information, such as to provide a waveform representing the cycle. Alternatively or additionally, lines from different frames of data in a sequence are used to generate an image. The image shows cycle timing information.

In a first aspect, a method is provided for determining cyclical information from ultrasound data. A sequence of frames of data each representing a two or three dimensional region is obtained. The data is transformed by projection, reducing an amount of data. Cycle timing information is determined as a function of the transformed data.

In a second aspect, a computer readable storage medium has stored therein data representing instructions executable by a programmed processor for determining cyclical information from ultrasound data. The storage medium has instructions for: transforming a sequence of frames of B-mode data each representing a heart, the transformation being by projection and reducing an amount of data; identifying first and second substantially maximum variance of the transformed data along first and second perpendicular dimensions, respectively; and determining a heart rate, an end diastolic frame of data, an end systolic frame of data or combinations thereof as a function of the B-mode data representing a location corresponding to the first and second substantially maximum variance.

In a third aspect, a system is provided for determining cyclical information from ultrasound data. A processor is operable to project data for each of a sequence of frames of data onto at least two dimensions, operable to identify a location as a function of the projected data, and operable to determine cycle information as a function of the data representing the location at different times. A display is operable to display the cycle information.

In a fourth aspect, a method is provided for determining cyclical information from ultrasound data. A sequence of frames of data each representing a two or three dimensional region is obtained. A line of the data is provided as a function of depth for each of the frames of data in the sequence. An image is generated from the lines for the sequence. The imaging is a function of time and depth.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A fully or partially automated approach to the ECG-free extraction of the end-systolic (ES), end-diastolic (ED) image frames or other timing information is provided. Using a Radon or other transform, the data is reduced to identify a location associated with substantial variance while reducing an amount of processing. The image data for the identified location is used to represent the cycle. After the ES and ED frames are detected, heart rate (beats per minute) is computed using the acquisition times, time-stamps or acoustic frame rate for the acquired image frames. The process is applied to various cardiac and other types of cycles, such as adult, fetal, neonatal or pediatric echocardiographic images. Two or three-dimensional imaging data acquired at different times may be used. The heart rate, ED frames, ES frames or other information is identified without prior or independent knowledge of the heart rate or gender of the patient.

Figure 1:
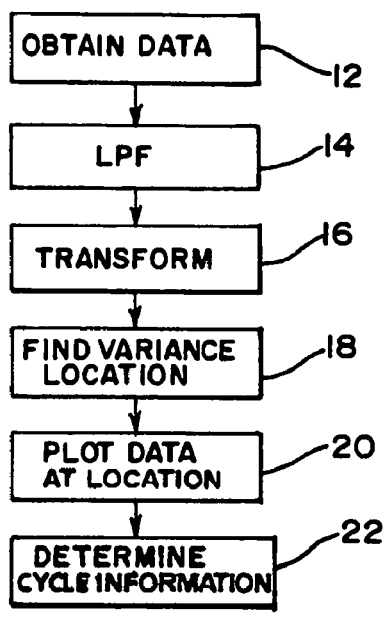
FIG. 1 is a flow chart diagram of one embodiment of a method for determining cyclical information.

FIG. 1 shows one embodiment of a method for determining cyclical information from ultrasound data. Additional, different or fewer acts may be provided. For example, acts 12, 16 and 22 are performed without act 14, 18, 20 or combinations thereof. The acts may be performed in a different order than shown. The cycle information resulting from this method is determined without or free of a reference image and/or an ECG signal. Alternatively, a reference image or ECG signal is used to verify results or to be used in obtaining the results, such as filtering two or more possible heart rates together.

In act 12, a sequence of frames of data is acquired. The data is image data, such as scan converted data, or detected data in a polar coordinates or acquisition format. For example, the data is scan converted B-mode data acquired in real time or recorded from a previous display. The frames of data each correspond to a single scan or signal set of data representing a two or three dimensional region. A frame of data representing the three-dimensional region is formatted on a reconstructed grid or as a plurality of different two-dimensional planes in a three-dimensional volume. For example, a sequence of frames of data for a 4D Fetal Heart clip is obtained with a slow, continuous or stepped, single sweep of a mechanical ultrasound transducer. The region is the heart, lungs, other organ, fluid region or other portion of a patient.

The sequence includes frames of data acquired at different times, such as associated with different time stamps. The sequence of frames of data is mathematically represented by:

$$J(x, y, n) = \{I(x, y, 1), I(x, y, 2), \ldots I(x, y, N)\}$$

where n=1, ..., N is the frame number in the set (t is the continuous time and n is its discrete counterpart) and (x, y) are the spatial coordinates of the pixels within the frame of data. The sequence represents a portion of a cycle or one or more cycles. In one embodiment, the (x, y) coordinates are defined with an origin at the top-left hand pixel in a corresponding image where the x-axis extends along the columns of the image and the y-axis extends along the rows of the image.

For cardiac imaging, the sequence of frames of ultrasound data represents the heart from standard echocardiographic views of the adult heart, such as a Parasternal Short Axis (PSAX), Apical-4-Chamber (A4C), Apical-2-Chamber (A2C), or Parasternal Long Axis (PLAX). Other views may be used. Each frame of data in the sequence is separated by about 33.33 milliseconds (in the illustrations) or other constant or variable time period. Alternatively, the sequence represents a fetal heart in a non-standard view or a standard echocardiographic view, such as a Short Axis (SAX), Apical-3-Chamber (A3C), or Apical-4-Chamber (A4C). The frames of data may be clipped, such as isolating data within the frames of data that contains the fetal heart and is free of other information, such as from the abdomen of the mother-to-be. For example, a region of interest is automatically or manually determined, and data outside the region is removed for processing.

The sequence of frames of data is acquired without substantial movement by the patient or fetus. Alternatively, the patient or fetus moves within the sequence, and the transformation and cycle determination are used to identify movement or undesired frames of data.

In act 14, the frames of data are spatially filtered. Each frame of data is low pass filtered, but band or high pass filtering may be used. The spatial filtering is performed prior to the transforming of act 16. In one embodiment, a Gaussian kernel is used on scan converted data representing a heart, but other kernels may be provided. To remove the effects of noise, each of the frames is smoothed by the Gaussian Kernel with a scale parameter a σ=3.0, resulting in a 7×7 window. Other scale parameters may be used, such as σ=1.0 for data in a polar coordinate format.

In act 16, the data is transformed. The transformation reduces the amount of data for determination of cycle information, resulting in less processing. Alternatively, the transform maintains a same amount of data or increases the data. A projective transform is applied, such as a Radon transformation. The data for each frame of data is projected onto two different dimensions, such as the orthogonal x and y axes. Non-orthogonal or dimensions other than the x and/or y axes may be used. A Radon Transform of an image I(x, y) on to the y-axis is mathematically defined as:

$$p(y) = \sum_x I(x, y). \tag{3}$$

The result of the transform for one frame of data representing a two dimensional region is a line along the y-axis with intensity modulated by the sum of each y-axis position throughout the frame of data. The radon transform p(y) of I(x, y) is the sum of all pixel values along each y (row of the image) over all or some x coordinates. Further, the radon transform of the set J on to the y-axis is given by:

$$p(y, n) = \sum_x I(x, y, n) \tag{4}$$

and that on to the x-axis is given by:

$$p(x, n) = \sum_y I(x, y, n). \tag{5}$$

Figure 2:
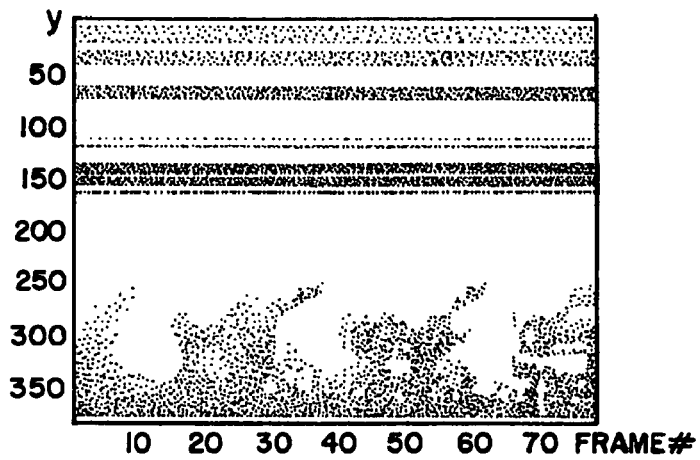
FIG. 2 is a graphical representation of one embodiment of data transformed along one dimension.
Figure 3:
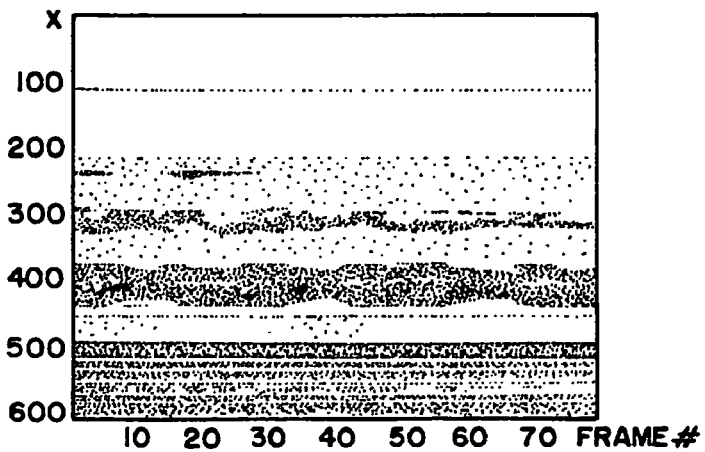
FIG. 3 is a graphical representation of one embodiment of data transformed along another dimension.

The transform is performed for one or both of the x and y axes. FIGS. 2 and 3 show the results of Radon transformation along the x and y axes, respectively. The vertical axis represents the row or column position and the horizontal axis is the frame number, n, within the sequence. The images of FIGS. 2 and 3 are examples derived from an A4C sequence of an adult heart.

In act 18, a location is identified from the transformed data. The location is used to determine cycle timing information. The location is identified as a substantially maximum variance along the x and/or y axes of the projected data. The location corresponds to a region that has the maximum gray level variance along the temporal axis (t or n) in the sequence. The line along the time or n-axis that has the maximum gray level variance in each projection is identified. The lines of maximum gray level variation provide the yn-plane and xn-plane in the original image set, J, along which the gray level varies maximally. The intersection of these two planes, $(\hat{x}, \hat{y}, n)$ is the line through the original image set, J, with maximum gray level variation. Identification of the location is mathematically expressed as follows:

$$\hat{x} = \arg_x \max(v(x)), \quad (6)$$

$$\hat{y} = \arg_y \max(v(y)), \quad (7)$$

where $v(x)$ and $v(y)$ are the gray level variances along x and y directions in the projection images $p(x,n)$ and $p(y,n)$, respectively, given by, $$v(x) = \frac{1}{\#p(x) - 1} \sum_n (p(x, n) - \overline{p}(x))^2, \quad (8)$$

$$v(y) = \frac{1}{\#p(y) - 1} \sum_n (p(y, n) - \overline{p}(y))^2, \quad (9)$$

and $\overline{p}(x)$, and $\overline{p}(y)$ are the sample means given by, $$\overline{p}(x) = \frac{1}{\#p(x)} \sum_n p(x, n), \quad (10)$$

$$\overline{p}(y) = \frac{1}{\#p(y)} \sum_n p(y, n), \quad (11)$$

and $\#p(x)$, and $\#p(y)$ are the total number of pixels along the n-axis in the $p(x,n)$ and $p(y,n)$, respectively. Other identifications of the location using the same or different variance parameter or a non-variance parameter may be used.

The location in the region with a relatively large variance throughout the sequence is identified from the transformed data. The location $(\hat{x}, \hat{y})$ corresponds to one of the left ventricular valve locations in the Adult heart sequence used for FIGS. 2 and 3. In the case of a PLAX view, the valve location at the septum may be identified. Other locations may be identified. This result may be further optimized, such as providing the location to an algorithm that utilizes this approximate localization to arrive at more robust valve localization result.

Figure 4:
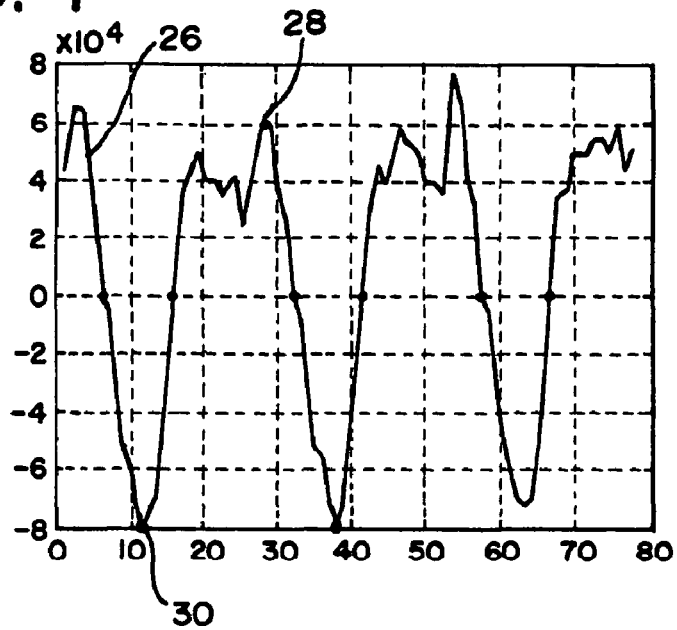
FIG. 4 is a graphical representation of one embodiment of an automatically determined cycle.

In act 20, the data associated with the identified location is plotted or used to determine cycle information without plotting or display. The data at the location as a function of time through the sequence represents the cycle. Cycle timing information is calculated from the data representing the location. For example, the ES and ED frames or times are identified. FIG. 4 shows a plot or graph of gray scale data 26 at location row 317 and column 435 through the sequence of images used for FIGS. 2 and 3. The gray scale data is B-mode data with values 0 to 255. The plot of gray scale values 26 is shifted. For example, the maximum and minimum along the plot are determined. The DC or mid-level gray scale value is shifted to zero. Other shifts or no shift may be used.

In act 22, cycle information is determined, such as determining the timing of events (ED and/or ES frame or time) and/or the heart rate. For example, the minima 30 in gray scale values 26 correspond to the ES frames, and the maxima 28 correspond to the ED frames. FIG. 4 shows the gray scale values without smoothing as a function of time. Alternatively, the plot is smoothed, such as by applying a low pass filter. Spatial smoothing may also be provided, such as using data representing a plurality of locations around the identified location. For example, an M×M boxcar filter around $(\hat{x}, \hat{y})$ is applied for each n. The smoothed or spatially filtered information is plotted as a function of time or frame number. The ES and ED frames are identified using this smoothed gray level line.

The heart rate is determined and displayed in one embodiment. For example, the heart rate is determined using one or more cyclical events, such as the ED or ES events. Heart rate is computed from the ES and ED frame locations with the temporal separation of or timestamps on each of the frames of data. For example, there are K heart cycles or R-R intervals detected. There are $N_1, N_2, \ldots, N_K$ number of frames (not all necessarily equal) in each R-R interval. The average R-R interval time (in milliseconds) is given by, $$T_{RR} = \frac{\sum_{i=1}^{N_1} T_i + \sum_{i=1}^{N_2} T_i + \ldots \sum_{i=1}^{N_K} T_i}{K}, \quad (12)$$

$$HR = \frac{60.0}{10^{-3} T_{RR}}, \quad (13)$$

where the denominator of equation (13) is in units of seconds.

As another example, the sequence includes only one R-R interval (i.e., there are two ED frames and one ES frame). In a split computation example, the frame times from ED to ES is summed and then doubled to calculate the heart cycle time. The frame times from ES to ED are summed and then doubled to calculate another value for the heart cycle time. These two heart cycle times are averaged or one is selected to get the final heart cycle time. This calculation is mathematically represented as:

$$T_{RR} = \frac{\left(2 \sum_{i=1}^{N_1} T_i + 2 \sum_{i=1}^{N_2} T_i\right)}{2} \quad (14)$$

where $N_1$ are the frames from ED to ES, and $N_2$ are the frames from ES to ED.

In a full computation example, the N frame times for the R-R interval are summed, providing a heart cycle time. This sum is mathematically represented as:

$$T_{RR} = \sum_{i=1}^{N} T_i \quad (15)$$

In a further example, the heart cycle times given by equations (14) and (15) are averaged to get the mean heart cycle time. Equation (13) is used to calculate the heart rate from the mean heart cycle time. In equation (14), the ES frame is considered twice in the numerator, once in the first summation and again in the second summation.

The cycle timing information is used for further processing or display. For example, the ED or ED frames are highlighted to the user. As another example, the plot representing the cycle is displayed to the user. As yet another example, the heart rate is continuously updated and displayed to the user as data is acquired.

In one embodiment, the acquired data is reordered based on the detected cardiac cycles to generate data sets for volumes for one or more cardiac cycles. For example, the cycle timing information is used as disclosed in U.S. Pat. No. 6,673,017, the disclosure of which is incorporated herein by reference, to increase temporal resolution. For 4D fetal echocardiography using a mechanical transducer, the cycle information is used to detect the ES frames of data. A single, slow continuous or stepped sweep of the transducer is used to acquire a large number of frames at a high frame rate. In case of stepped acquisition of fetal heart data, multiple image frames are acquired at each step to ensure one or more cardiac cycles are captured. At each step, the algorithm described in this herein is applied to detect the ES, ED frames and/or heart rate. Using this information, the data is then reordered into a cogent data set containing fetal heart volumes for one or more cardiac cycles. The volumes are then rendered and displayed as a 4D sequence.

In yet another embodiment, the cycle information is used for any purpose with other sources of ECG information, such as disclosed in application Ser. No. 10/876,189pending, the disclosure of which is incorporated herein by reference.

In one embodiment, the cycle information is used to determine the ejection fraction (EF). For example, the left ventricular EF is computed from the endocardial boundaries of the left ventricle in the ED and ES frames of data. The detected the ED and ES frames of data are used for one or more cardiac cycles.

In another embodiment, the cycle information provides a fetal heart rate or ECG type waveform. Rather than manual identification of ED and ES frames of data by sonographers or cardiologists, the fetal heart rate or waveform is quantified automatically.

The cycle information is used in other embodiments to detect errors or events. Where the cycle or temporal separation of ED and/or ES frames varies by a threshold amount, the frames of data associated with the variation may be discarded or used to indicate the event. For example, the plot of the gray scale data for a location may become erratic, indicating movement of a baby being imaged.

For A4C, A2C and PLAX views, the location identified for determining the cycle information is the left ventricular valve or the valve leaflet. The location is highlighted or otherwise indicated to allow or assist in tracking of one of the valve points.

Figure 5:
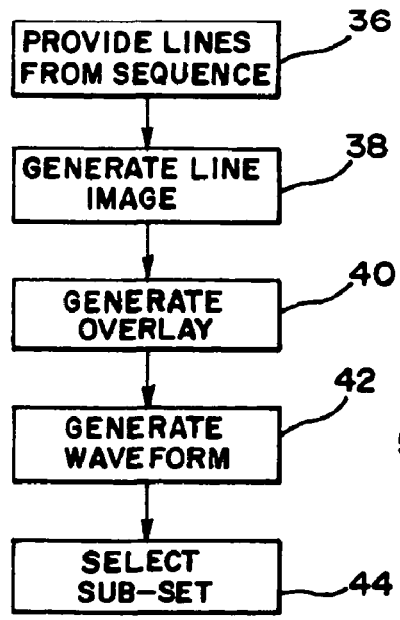
FIG. 5 is a flow chart diagram of another embodiment of a method for preparing and displaying the cyclical information as a feedback mechanism.

FIG. 5 shows a method for determining cycle information. The method of FIG. 5 is used in addition or as an alternative to the method of FIG. 1. Additional, different or fewer acts may be provided, such as performing acts 36 and 38 without acts 40, 42, and/or 44. The acts are performed in the same or different order.

In act 36, at least one line showing data as a function of depth is provided for each of the frames of data in the sequence. The line extends along the depth or range dimension with a same lateral position. Alternatively, the line extends along at an angle or any orientation relative to the region represented by the frame of data. The data closest to the line is selected, used for interpolation or otherwise combined to determine data for the line. In one embodiment, a center line or group of lines is selected from each frame of data in the sequence. In another embodiment, a line derived using the transform or projection discussed above is used. The projection along a lateral axis is selected, such as shown for one frame of data in FIG. 2.

Figure 6:
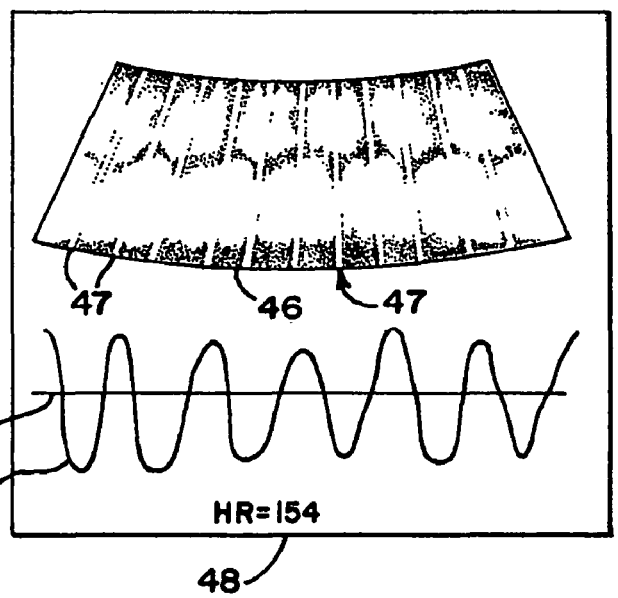
FIG. 6 is a graphical representation of one embodiment of a display of cyclical information.

In act 38, an image is generated as a function of time and depth. The image is generated from data from each or a sub-set of the images of the sequence. The lines of data from the frames of data are combined to form an image. FIG. 6 shows a two-dimensional image 46 where each line along a lateral axis in a sector type format corresponds to a different frame of data. Similarly, FIG. 2 shows a two-dimensional image where each projected line along a lateral axis in a linear type format corresponds to a different frame of data. B-mode data is used, but other types of data (e.g., velocity or flow energy or power) may alternatively or additionally be used. The user may toggle between overlaying flow data and not on the B-mode data.

The image 46 provides feedback to ensure a complete or desired data set is acquired, such as for sweeping a region for three or four dimensional imaging. For example, the image 46 is generated in real time during acquisition where data from newly acquired frames of data are added to the previous image 46. The image 46 is displayed in any desired orientation, such as inverted up-down and/or left-right.

The image 46 enables the user to cancel the acquisition at any time, without wasting time in waiting for the acquisition to be completed and the acquired dataset to be rendered and displayed. For example, if the patient, such as a baby, moves, the image 46 may show an irregularity, indicating that the scan should be stopped. The user cancels the acquisition at any time by pressing a hardware or software button/key or by mouse selection.

Other user interactive displays may be provided. For example, a pop-up window, buttons or other information is displayed for selection by the user. The user edits frame locations, such as ED or ES frame locations shown as lines 47. The user accepts the acquired data as being sufficient for subsequent processing or display or cancels the acquisition in favor of repeating the attempt at acquiring data for an examination.

In optional act 40, an overlay is generated on the image 46. The overlay indicates the cycle timing or other information. The overlay contains lines, color overlays and/or symbols. For example, cycle timing information determined as discussed above for FIG. 1 or in another method is used to identify ED and/or ES frames of data. A blank line 47 is inserted in the image 46 as an overlay to indicate the detected frames. Alternatively, a colored line is overlaid on the data for the detected frames. In other embodiments, a color, brightness, hue or other characteristic is altered for groups of frames of data, such as overlaying red for systolic and blue for diastolic frame of data. The image 46 has a repeating pattern of red and blue indicating the phases of the cycle. The user may be able to configure the overlay, such as color choices, transparency levels, or symbols. Alternatively or additionally, the system automatically configures the overlay.

In optional act 42, a waveform 50 is displayed. The waveform represents cycle information, such as the plot of gray scale values 26. The waveform 50 is a function of the acquired data, but may be derived from other sources, such as an ECG input. The waveform 50 may be color coded or include overlays or symbols corresponding to any overlays of act 40.

In optional act 44, a sub-set of the sequence is selected in response to user input designating a portion of the image 46.

The user delineates a portion of the image 46 with a mouse or trackball. The delineated portion represents frames of data to be used or excluded from subsequent processing. In a multi-cycle acquisition, if the user cancels the acquisition between 1 to N cardiac cycles, the user has the option of salvaging the useful data as opposed to erasing all the data and starting over.

Figure 7:
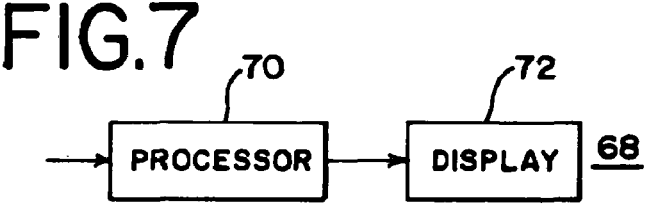
FIG. 7 is a block diagram of one embodiment of a system for determining cyclical information.

FIG. 7 shows one embodiment of a system 68 for determining cyclical information from ultrasound data. The system 68 includes a processor 70 and a display 72. Additional, different or fewer components may be provided. For example, a transducer and beamformers connect with the processor 70. In one embodiment, the system 68 is a medical diagnostic ultrasound imaging system. Other medical or non-medical imaging systems may be used. In another embodiment, the system 68 is a computer, workstation, laptop or other data processing device for generating images from stored or transferred data.

The processor 70 is a general processor, control processor, application-specific integrated circuit, field-programmable gate array, digital circuit, analog circuit, digital signal processor, combinations thereof, or other now known or later developed devices for determining cycle information. A computer-readable storage media or memory, such as a cache, buffer, RAM, removable media, hard drive or other computer-readable storage media, connects with the processor 70. Computer-readable storage media include various types of volatile and non-volatile storage media. The functions, acts or tasks illustrated in the figures or described herein are performed by the processor 70 executing instructions stored in or on the computer-readable storage media. The functions, acts or tasks are independent of the particular type of instructions set, storage media, processor or processing strategy and may be performed by software, hardware, integrated circuits, film-ware, microcode and the like, operating alone or in combination. Likewise, processing strategies may include multi-processing, multi-tasking, parallel processing and the like. In one embodiment, the instructions are stored on a removable media device for reading by a medical diagnostic imaging system. The imaging system uploads the instructions for performing the acts discussed herein. In another embodiment, the instructions are stored in a remote location for transfer through a computer network or over telephone lines to an imaging system or workstation. In yet other embodiments, the instructions are stored within the imaging system or workstation.

The processor 70 obtains frames of data and implements one or both of the methods described above with respect to FIGS. 1 and 5. For example, the processor 70 is operable to project data for each of a sequence of frames of data onto at least two dimensions, identify a location as a function of the projected data, and determine cycle information as a function of the data representing the location at different times. The processor 70 uses the cycle information for further processing or to generate an image with or without an overlay. The display 72 receives image information and is operable to display the information, such as the heart rate, ED timing, ES timing, overlays or other cycle information.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A non-transitory computer readable storage medium having stored therein data representing instructions executable by a programmed processor for determining cyclical information from ultrasound data, the storage medium comprising instructions for:
   obtaining a sequence of frames of data each representing data of a same two or three dimensional region acquired at a different time;
   transforming the data sequence by projection along different spatial dimensions, the transformation reducing an amount of data; and
   determining cycle timing information as a function of the transformed data sequence;
   wherein determining comprises:
   identifying from the transformed data sequence a location in the region having with a relatively large variance, wherein the location is identified by identifying a line extending in a temporal dimension of the sequence of frames, the line being an intersection of first and second planes extending along different spatial dimensions of the region and extending along the temporal dimension, the different spatial dimensions comprising dimensions used for the transforming, and the first and the second planes being identified by determining a first and a second spatial lines of said sequence projected along a first and a second of said different spatial dimensions, respectively, said first and second lines having a maximum variance in their respective projected sequences; and
   calculating cycle timing information from data representing the location.

2. The method of claim 1 wherein obtaining comprises obtaining B-mode data representing a heart over at least one cycle and wherein determining cycle timing information comprises determining a heart rate, an end diastolic frame of data, an end systolic frame of data or combinations thereof.

3. The method of claim 1 wherein transforming the data sequence comprises performing a Radon transformation.

4. The method of claim 1 wherein transforming the data sequence comprises projecting the data for each frame of data onto a first dimension and onto a second dimension, the first dimension different than the second dimension, projecting being collapse of a single two dimensional image into a one dimensional line.

5. The method of claim 4 wherein determining further comprises:
   identifying first and second maximum variance of the projected data sequence along the first and second dimensions, respectively; and
   using the data representing the location corresponding to the first and second maximum variance as indicative of the cycle timing.

6. The method of claim 1 wherein determining the cycle timing information comprises determining a frame of data associated with a cyclical event.

7. The method of claim 6 wherein determining the cycle timing information comprises determining a heart rate as a function of the cyclical event.

8. The method of claim 1 further comprising:
   spatially filtering the data of the sequence prior to the transforming.

9. The method of claim 1 further comprising:
   providing a line showing data as a function of depth for each of the frames of data in the sequence; and
   generating an image as a function of time and depth, the image comprising each line.

10. The method of claim 1 wherein the transforming and determining are performed free of a reference image and an ECG input.

11. A non-transitory computer readable storage medium having stored therein data representing instructions executable by a programmed processor for determining cyclical information from ultrasound data, the storage medium comprising instructions for:
    transforming a sequence of frames of B-mode data each representing a heart, the transformation being by projection and reducing an amount of data;
    identifying first and second substantially maximum variance of the transformed data along first and second perpendicular dimensions, respectively, the first and second perpendicular dimensions being spatial dimensions in each of the frames of the sequence, the first and second substantially maximum variance defining plane locations for first and second respective planes orthogonal to each of the respective first and second perpendicular dimensions; and
    determining a heart rate, an end diastolic frame of data, an end systolic frame of data or combinations thereof as a function of the B-mode data representing a spatial location represented in the sequence of frames and corresponding to an intersection of the first and second planes with the plane locations defined by the first and second substantially maximum variance, wherein variance comprises a measure of change for each dimension, a different measure provided for each dimension, the spatial location at the intersection associated with a substantially maximum variance in time through the sequence.

12. The instructions of claim 11 wherein transforming the data comprises performing a Radon transformation.

13. The instructions of claim 11 further comprising:
    spatially filtering the B-mode data of the sequence prior to the transforming.

14. The instructions of claim 11 further comprising:
    providing a line showing data as a function of depth for each of the frames of data in the sequence; and
    generating an image as a function of time and depth, the image comprising each line.

15. The instructions of claim 11 wherein the transforming and determining are performed free of a reference image and an ECG input.

16. A system for determining cyclical information from ultrasound data, the system comprising:
    a processor configured to project data for each frame of a sequence of frames of data onto at least two dimensions, the data for each of the frames representing an area, the projection for one of the at least two dimensions being performed separately from the projection for another of the at least two dimensions, operable to identify a location represented by each of the frames and as a function of the projected data based on variance along the one and the other dimensions, the location corresponding to an intersection of lines from the one and the other dimensions, the lines located along the one and other dimensions based on the variance, and configured to determine cycle information as a function of the data representing the location at different times, the location comprising a single pixel; and
    a display configured to display the cycle information.

17. The system of claim 16 wherein the data comprises B-mode data representing a heart over at least one cycle, wherein the processor is configured to project the data by performing a Radon transformation, and wherein the cycle information comprises a heart rate, an end diastolic frame of data, an end systolic frame of data or combinations thereof.

18. The system of claim 16 wherein the processor is configured to determine the cycle information by:
    identifying first and second maximum variance of the projected data along the first and second dimensions, respectively;
    wherein the location corresponds to the first and second maximum variance.

19. The system of claim 16 wherein the processor is configured to project, identify the location and determine the cycle information free of a reference image and an ECG input.

20. A non-transitory computer readable storage medium having stored therein data representing instructions executable by a programmed processor for determining cyclical information from ultrasound data, the storage medium comprising instructions for:
    obtaining a sequence of frames of data each representing a two or three dimensional region;
    providing a line of the data as a function of depth for each of the frames of data in the sequence, each line of data having values for different depths for each frame;
    generating an image from the lines for the sequence, the generating being a function of time and depth, the image comprised of the lines from the frames of data in the sequence such that the lines from the sequence are spaced along a time axis and each line includes the values for a depth axis; and
    calculating cycle timing information from the generated image of the lines.

21. The method of claim 20 wherein providing the line for each of the frames of data comprises selecting a center line in each of the frames of data.

22. The method of claim 20 wherein providing the line for each of the frames of data comprises projecting the data of each frame along a lateral axis.

23. The method of claim 20 further comprising:
    determining cycle timing information as a function of the data; and
    generating an overlay on the image indicating the cycle timing.

24. The method of claim 20 further comprising:
    displaying a waveform, the waveform being a function of the data.

25. The method of claim 20 wherein obtaining comprises scanning sequentially along a plurality of different two-dimensional planes in a three-dimensional volume.

26. The method of claim 20 further comprising:
    selecting a sub-set of the sequence in response to user input designating a portion of the image.

* * * * *